US012751446B2

(12) United States Patent
Wieland

(10) Patent No.: US 12,751,446 B2
(45) Date of Patent: Oct. 6, 2026

(54) AQUEOUS SOLUTION FOR CELL PRESERVATION

(71) Applicant: PromoCell GmbH, Heidelberg (DE)

(72) Inventor: Hagen Wieland, Heidelberg (DE)

(73) Assignee: PromoCell GmbH, Heidelberg (DE)

( * ) Notice: Subject to any disclaimer, the term of this patent is extended or adjusted under 35 U.S.C. 154(b) by 727 days.

(21) Appl. No.: 17/850,687

(22) Filed: Jun. 27, 2022

(65) Prior Publication Data

US 2022/0408718 A1 Dec. 29, 2022

(30) Foreign Application Priority Data

Jun. 29, 2021 (DE) ..................... 10 2021 116 694.2

(51) Int. Cl.
*A01N 1/125* (2025.01)
*A61K 35/12* (2015.01)

(52) U.S. Cl.
CPC .............. *A01N 1/125* (2025.01); *A61K 35/12* (2013.01)

(58) Field of Classification Search
CPC ................................ A01N 1/125; A61K 35/12
See application file for complete search history.

(56) References Cited

U.S. PATENT DOCUMENTS

| | | | | |
|---|---|---|---|---|
| 8,865,240 | B2 * | 10/2014 | Paulsen | A61K 9/0087 426/392 |
| 2006/0246042 | A1 | 11/2006 | Davies | |
| 2010/0216237 | A1 | 8/2010 | Ganchas Soares et al. | |
| 2016/0041083 | A1 * | 2/2016 | Wanders | G01N 33/49 435/39 |
| 2016/0081917 | A1 | 3/2016 | Ra et al. | |
| 2019/0153396 | A1 | 5/2019 | Wieland | |
| 2019/0194621 | A1 | 6/2019 | Yamaguchi et al. | |

FOREIGN PATENT DOCUMENTS

| | | | | | |
|---|---|---|---|---|---|
| EP | 1 950 283 | B1 | 7/2015 | | |
| JP | 2002530293 | A | 9/2002 | | |
| JP | 2010273549 | A | 12/2010 | | |
| JP | 2010539970 | A | 12/2010 | | |
| JP | 2016519142 | A | 6/2016 | | |
| JP | WO2018/047941 | A1 | 3/2018 | | |
| JP | 2019506878 | A | 3/2019 | | |
| JP | 7515539 | B2 | 7/2024 | | |
| WO | WO2017/123465 | * | 7/2017 | | A01N 1/02 |
| WO | WO2018/232110 | * | 12/2018 | | A01N 1/02 |
| WO | WO2021/041399 | * | 3/2021 | | A01N 1/02 |

OTHER PUBLICATIONS

Applied Biosystems | Ambion, (Catalog #: AM9624—500ml amount AM9625—1L amount): 10x PBS pH 7.4 | Retrieved on Sep. 19, 2024 at: https://assets.thermofisher.com/TFS-Assets/LSG/manuals/sp_9625.pdf (Year: 2008).*

Maity et al., Use of hydrocolloids as cryoprotectant for frozen foods Critical Reviews in Food Science and Nutrition 2018, vol. 58, No. 3, 420-435.*

Sigma Product number Phenol Red sodium salt-power p. 1 downloaded Aug. 25, 2025.*

Sigma Product No. G7021 D-(+)-Glucose powder, BioReagent, suitable for cell culture p. 1 downloaded Aug. 25, 2025.*

Sigma Product No. G6013 L-Glutathione p. 1 downloaded Aug. 25, 2025.*

Sigma Product No. C6852 L-Cysteine hydrochloride monhydrate p. 1 downloaded Aug. 25, 2025.*

Sigma Product No. A8960 L-Ascorbic acid 2-phosphate p. 1 downloaded Aug. 25, 2025.*

Hottot et al Freeze drying of pharmaceuticals in vials: Influence of freezing protocol and sample configuration on ice morphology and freeze-dried cake texture Chemical Engineering and Processing 46 (2007) 666-674.*

Yang et al Intracellular ice formation and growth in MCF-7 cancer cells ; Cryobiology vol. 63, Issue 1, Aug. 2011, pp. 38-45.*

JP Patent Application No. JP2022-100286, Office Action issued Sep. 28, 2023, 5 pages (with English language translation).

* cited by examiner

*Primary Examiner* — Teresa E Knight
*Assistant Examiner* — Michael Angelo Riga
(74) *Attorney, Agent, or Firm* — Mueting Raasch Group

(57) ABSTRACT

The invention relates to an aqueous solution for cell preservation of preferably mammalian cells, which can be used for cell preservation as a cryoprotectant or as a pharmaceutical product or excipient. Furthermore, the invention relates to a method for preserving cells using the aqueous solution for cell preservation, and to a method for defrosting cells which are frozen in the aqueous solution.

14 Claims, No Drawings

AQUEOUS SOLUTION FOR CELL PRESERVATION

PRIORITY CLAIM

This application claims priority to German Application No. 10 2021 116 694.2, filed Jun. 29, 2021, wherein the contents of said application is incorporated herein by reference in its entirety.

FIELD OF THE INVENTION

The present invention relates to an aqueous solution for the cell preservation of preferably mammalian cells. The present invention further relates to the use of the aqueous solution according to the invention for cell preservation as a cryoprotectant or for use as a pharmaceutical product or excipient. Furthermore, the present invention relates to a method for preserving cells using the aqueous solution according to the invention for cell preservation, and to a method for defrosting cells which are frozen in the aqueous solution according to the invention.

STATE OF THE ART

The cryopreservation of mammalian cells can in principle be carried out in two different ways, which differ in terms of the speed of the freezing process, namely so-called "slow freezing" and vitrification.

Slow Freezing (Temperature Drop 0.3 to 10° C. Per Minute)

A prime example of the simplest variant of this method used in the academic sector, freezing without a controlled freezing rate, is the widespread "Mr. Frosty": The structure of the vessel and the filling with isopropanol ensure a relatively uniform cooling of the cells at approximately 1° C. per minute, i.e. a passive but uniform freezing process, in dry ice or a −80° C. freezer. Nevertheless, this type of cooling cannot be referred to as controlled since external influences (position in the dry ice container), opening of the −80° C. freezer, etc.) cannot be ruled out. The results that can be achieved with this type of freezing device during the cryopreservation of mammalian cells are often sufficient for routine applications—although not optimal. Due to the low cost of materials, this method is the most prevalent method used in research.

Freezing with a controlled freezing rate (defined but variable temperature drop/time), so-called "controlled rate slow-freezing", is widespread in the industrial sector or in cell banks. The cells resuspended in freezing medium are frozen in a computer-controlled manner at a controlled (but not necessarily constant) cooling rate. As well as the standardized conditions, optimal results are achieved by a change in the temperature profile during the freezing process. While cooling to the critical phase with potential formation of harmful ice crystals ("supercooling") takes place slowly at 1-3° C. per minute, the samples are cooled more quickly after passing through this phase at about 10° C. per minute. Ideally, a target/actual comparison is carried out between the sample temperature and the target temperature via several probes. In particular, in the commercial/industrial cryopreservation of cells, controlled slow freezing is the most frequently used method since, in addition to the physico-technical advantages, it additionally offers the best possibilities for standardizing and mechanically logging each freezing process.

Vitrification ("Flash-freezing"; Uncontrolled Temperature Drop: Several Hundred ° C. per Second).

Vitrification (Latin for "glazing") is understood to mean the rapid freezing of biological samples in liquid nitrogen. Above all, vitrification is customary in the cryopreservation of sperm, egg cells and embryos, but recently also in the case of some pluripotent stem cells. In this case, the sample material is not filled in cryovials, but in so-called "straws", thin tubes made from a special plastic and welded on both sides. As a result of the extremely rapid cooling, the samples solidify in fractions of seconds in an amorphous, vitreous state, without harmful crystals forming. The advantage of the method is that it can also be used "in the field" or in other areas without complex laboratory or cryotechnology by means of liquid nitrogen. For this reason, it was previously used primarily in reproductive medicine (human/animal) and, as a result, was primarily optimized for these applications.

The limitations of vitrification are that it is only suitable for samples with very small volumes up to about 200 μl, and that, due to the high cryoprotectant (CPA) content in the vitrification medium, the thawing process is very much more critical than for cryomedia for slow freezing [2]. In addition, the technique as such offers a high potential for standardization, but the fact that machine logging of the freezing process is not possible is a disadvantage. Therefore, the prevalence of this method in the scientific and industrial sectors is comparatively low.

Storage of Cryopreserved Cells/Samples by Means of "Slow Freezing"

During the cryopreservation process, the samples are cooled to −80 to −90° C. However, the freezing process is not yet completed at this point since the so-called "glass transition", i.e. the complete solidification of the CPA mixture in the form of a glass-like, amorphous and crystalline composition, only takes place at about −130° C. In reality, therefore, the freezing process is only terminated by the transfer of the cells from the freezer into the liquid nitrogen [3].

The critical factor here is that the cells are damaged slowly, but with constant progress, by the formation of ice crystals at all temperatures above −130° C. This phenomenon is also the reason why cryopreserved cells lose viability and functionality when stored at −80° C., even if this is done without interruption. Intact tissue pieces can be stored below −130° C. for years while maintaining their biological functionality, while storage at −100° C. results in a gradual loss of function within 2 years. If such heating processes follow temporarily and cyclically during the storage period, for example due to certain events that occur regularly, the harmful effects accumulate. For this reason, when storing cryopreserved cells over the long term, care should be taken to minimize exposure to temperatures above −130° C. as much as possible [3].

Although the prior art knows of different media for preserving cells, these media have one disadvantage or another, e.g. only a small number of cells grow after thawing or the thawed cells grow very slowly.

There is therefore a need for further, ideally improved, media for preserving cells, which ideally facilitate gentle cryopreservation, that is to say, in particular, facilitate freezing with minimal loss of vitality and viable cell count or gentle thawing with a high survival rate.

OBJECT

The object underlying the present invention is to provide ideally improved media for preserving cells.

The underlying object is achieved by the subject matter of the claims, the embodiments described herein or the examples.

OBJECT OF THE INVENTION

The underlying invention relates to an aqueous solution for cell preservation, comprising

- potassium chloride,
- potassium phosphate, preferably monobasic anhydrous potassium phosphate
- sodium chloride,
- sodium phosphate, preferably dibasic anhydrous sodium phosphate,
- glucose, preferably anhydrous D(+)-glucose,
- ascorbic acid, preferably magnesium-L-ascorbate-2-phosphate,
- cysteine, preferably L-cysteine HCl x $H_2O$,
- glutathione, preferably reduced glutathione,
- methyl cellulose, and
- dimethylsulfoxide (DMSO).

"Cell preservation" or "preservation of cells" preferably involves cell cryopreservation or cryopreservation of cells. Cryopreservation is understood to mean a usually long-term storage of cells below 0° C., in particular at −20° C. to −200° C. The freezing is generally carried out at 1° C./min.

The present invention preferably relates to an aqueous solution according to the invention for cell preservation, comprising

- 0.0185% w/v potassium chloride,
- 0.0185% w/v potassium phosphate, preferably monobasic anhydrous potassium phosphate
- 0.8695% w/v sodium chloride,
- 0.1064% w/v sodium phosphate, preferably dibasic anhydrous sodium phosphate,
- 0.0925% w/v glucose, preferably anhydrous D(+) glucose anhydrous,
- 0.1203% w/v ascorbic acid, preferably magnesium-L-ascorbate 2-phosphate, 0.0028% w/v cysteine, preferably L-cysteine HCl x $H_2O$,
- 0.0925% w/v glutathione, preferably reduced glutathione,
- 0.1013% w/v methyl cellulose, and 8.25% w/v DMSO.

In a particularly preferred embodiment, the aqueous solution according to the invention for preserving cells is prepared as follows:

| | [mg/L] |
|---|---|
| Potassium chloride | 185 |
| Potassium phosphate, monobasic anhydrous | 185 |
| Sodium chloride | 8695 |
| Sodium phosphate, dibasic anhydrous | 1064 |
| D(+) glucose, anhydrous | 925 |
| Magnesium-L-ascorbate-2-phosphate | 1203 |
| L-cysteine HCl × $H_2O$ | 28 |
| Glutathione, reduced | 925 |
| Methyl cellulose | 1013 |
| DMSO | 82500 |

The aqueous solution for cell preservation according to the invention is preferably used for "slow freezing" methods for preserving cells. Preferably, the aqueous solution for cell preservation according to the invention is not used for methods that apply vitrification.

Preferably, the aqueous solution for cell preservation according to the invention can further comprise phenol red, preferably phenol red sodium salt.

The aqueous solution for cell preservation according to the invention preferably further comprises cells that are to be preserved. These cells to be preserved are preferably mammalian cells. The term "cell" or "cells" also comprises cell aggregates.

Preferred mammalian cells are lymphocytes, spleen cells, thymocytes, animal cells, somatic stem cells, mesenchymal stem cells, non-human embryonic stem cells, induced pluripotent stem cells, or cancer stem cells.

Particularly preferred mammalian cells are human induced pluripotent stem cells (hipSC), human mesenchymal stem cells from bone marrow (hMSC-BM), human mononuclear cells from peripheral blood (hMNC-PB/PBMC), human dermal fibroblasts from adult skin (NHDF-a), human dermal melanocytes from adult skin (NHEM-a) or human smooth muscle cells from the aorta (HAoSMC).

Further particularly preferred mammalian cells are human cancer cell lines, for example the human breast cancer cell line MCF-7.

The cells to be preserved can be both cells which are freshly isolated from tissue or cells which have already been cultured or expanded in vitro.

The cell count per milliliter of cell suspension that is to be preserved is preferably between 100,000 and 100 million cells.

Preferably, cells are separated from their culture or isolation medium/buffer before they are preserved with the aid of the aqueous solution according to the invention for preserving cells. All work is preferably carried out under sterile conditions.

The present invention further relates to the use of the aqueous solution according to the invention for cell preservation as a cryoprotectant.

The present invention likewise relates to an aqueous solution according to the invention for cell preservation for use as a medicament or excipient.

Furthermore, the present invention relates to a method for preserving cells, comprising (a) dispersing cells in the aqueous solution according to the invention for cell preservation in a container; and (b) feeding the container to cryopreservation.

Further, the present invention relates to a method for defrosting cells that are dispersed and frozen in the aqueous solution according to the invention for cell preservation, comprising (a) thawing a container in which the frozen cells are dispersed and frozen in the aqueous solution of the invention for cell preservation; and (b) adding the thawed cells to a culture medium suitable for the cells.

EXAMPLES

Materials Used

| Order No. | Name | Supplier |
|---|---|---|
| M7140 | Methyl cellulose | Sigma |
| D4540 | DMSO | Sigma |
| A8960 | L-Ascorbic Acid 2-Phosphate Mg | Sigma |
| C6852 | L-Cysteine × HCl × H2O | Sigma |
| G6013 | Glutathione (reduced) | Sigma |
| G7021 | D(+)-Glucose anhydrous | Sigma |
| 207790250 | Sodium Chloride | Acros/ Fisher |
| P5530 | Phenolic Sodium Salt optional for version with Phenol Red | Sigma |
| P0750-N10L | Dulbecco's Phosphate Buffered Saline w/o Ca/Mg (powder) | Biowest |
| | Potassium Chloride | |
| | Potassium Phosphate Monobasic Anhydrous | |
| | Sodium Chloride | |
| | Sodium Phosphate Dibasic Anhydrous | |

Example 1: Separating the Cells to be Frozen From Their Culture Medium

Both adherent growing cells and non-adherent cells growing in suspension can be frozen. The term "cells" here refers to individual cells and cell aggregates from up to several hundred cells.

Example 1A: Detaching Adherent Growing Cells

In order to detach adherent growing cells, the culture medium is first drawn off by suction. Then the cell layer is washed twice with a generous amount of PBS buffer (without $Ca^{2+}/Mg^{2+}$) and also drawn off by suction again. After addition of a suitable release agent, e.g., Accutase (https://www.accutase.com/accutase.html) or Trypsin-EDTA/TNS, the cells are detached according to the manufacturer's specifications. The detachment process is monitored microscopically. As soon as the cells begin to round off, they are detached completely by knocking lightly on the cell culture container. The detached cells are transferred into a sample tube and the concentration and total number of cells are determined by means of cell counting After pelleting the cells by centrifugation (e.g. for 3 minutes at 300×g and room temperature), the supernatant is cautiously drawn off by suction. Remaining in the sample tube is the cell pellet, which is subjected to further treatment as described in Example 2.

Example 1B: Harvesting Non-adherent Suspension Cells

Cells present or growing in suspension are transferred together with medium into a tube. The concentration and total number of cells are then determined by means of cell counting. After pelleting the cells by centrifugation (e.g. for 3 minutes at 300×g and room temperature), the supernatant is cautiously drawn off by suction. Remaining in the sample tube is the cell pellet, which is subjected to further treatment as described in Example 2.

Example 2: Freezing Cells With the Aqueous Solution According to the Invention for Cell Preservation The cell pellet produced in Example 1 is absorbed at room temperature in a corresponding amount (see below) of the aqueous solution according to the invention for cell preservation and resuspended by means of careful pipetting up and down using a serological pipette. The cell count per milliliter of cell suspension should be between 100,000 and 100 million cells. 1 ml of the cell suspension is rapidly distributed to freezing tubes in each case.

The tubes are then transferred without delay into a computer-controlled freezer (IceCube 14M). This has two reference temperature probes (a sample probe and one for the freezing chamber of the machine) which are positioned accordingly before the start of the freezing process. Thereafter, the controlled automatic freezing process is started with a suitable freezing protocol. The freezing process is complete when the samples have reached a temperature of ≤−80° C.

Alternatively, the cells can be cryopreserved on dry ice for at least 4 hours in freezing containers filled with 2-propanol, e.g. "Mr. Frosty".

The tubes with the frozen cells are subsequently removed from the freezer or the freezer container. They are transported on dry ice at −80° C. to the storage location, without interruption of the cooling chain, and are temporarily stored in liquid nitrogen. They can be kept there indefinitely.

The aqueous solution according to the invention for preserving cells is prepared as follows:

| | [mg/L] |
|---|---|
| Potassium chloride | 185 |
| Potassium phosphate, monobasic anhydrous | 185 |
| Sodium chloride | 8695 |
| Sodium phosphate, dibasic anhydrous | 1064 |
| D(+) glucose, anhydrous | 925 |
| Magnesium-L-ascorbate-2-phosphate | 1203 |
| L-cysteine HCl × $H_2O$ | 28 |
| Glutathione, reduced | 925 |
| Methyl cellulose | 1013 |
| Dimethylsulfoxide (DMSO) | 82500 |

Example 3: Thawing and Seeding Cells

A tube is initially charged with 9 ml of culture medium (room temperature). Furthermore, a suitable culture vessel is filled with a corresponding amount of culture medium (e. g., 0.2 to 0.3 ml/cm of heparin in the culture area) and this culture vessel is pre-equilibrated in the incubator at 37° C. and 5% $CO_2$ for at least 30 minutes.

The tube with the cryopreserved cells is removed from the liquid nitrogen and transported on dry ice. Thawing takes place for 2 minutes by means of a continuous pivoting movement in a temperature-controlled water bath at 37° C. The tube is disinfected with 70% (v/v) ethanol and transferred under the sterile bench. There, the tube with the thawed cells is opened and the cells are rapidly transferred into the 9 ml culture medium placed in a tube. Optionally, the viable cell count can be determined at this point in order to determine the exact cell count required for the optimal seeding density.

Thereafter, the cells are pelleted by means of centrifugation (for example for 3 minutes at 300×g and room temperature) and the supernatant is drawn off by suction. The cell pellet is absorbed in a suitable amount of fresh culture medium and the cell suspension (taking into account the recommended seeding density for the respective cell type) is transferred into the pre-equilibrated culture container. Further incubation takes place in the incubator at 37° C. and 5% $CO_2$.

The invention claimed is:

1. An aqueous solution for cell preservation, comprising 0.0185% w/v of potassium chloride,
0.0185% w/v of potassium phosphate,
0.8695% w/v of sodium chloride,
0.1064% w/v of sodium phosphate,
0.0925% w/v of glucose,
0.1203% w/v of ascorbic acid,
0.0028% w/v of cysteine,
0.0925% w/v of glutathione,
0.1013% w/v of methyl cellulose, and
8.25% w/v of dimethylsulfoxide (DMSO).

2. The aqueous solution for cell preservation according to claim 1, further comprising phenol red.

3. The aqueous solution of claim 2, wherein the phenol red is phenol red sodium salt.

4. The aqueous solution for cell preservation according to claim 1, further comprising mammalian cells that are to be preserved.

5. The aqueous solution for cell preservation according to claim 4, wherein the mammalian cells are selected from the group consisting of human induced pluripotent stem cells (hipSC), human mesenchymal stem cells from bone marrow (hMSC-BM), human mononuclear cells from peripheral blood (hMNC-PB/PBMC), human dermal fibroblasts from adult skin (NHDF-a), human dermal melanocytes from adult skin (NHEM-a) or human smooth muscle cells from the aorta (HAoSMC), and human cancer cell lines.

6. The aqueous solution of claim 5, wherein the human cancer cell lines comprise human breast cancer cell line MCF-7.

7. A method for preserving cells comprising (a) dispersing mammalian cells in the aqueous solution for cell preservation according to claim 1 within a container; and (b) feeding the container to cryopreservation.

8. A method of defrosting mammalian cells, comprising (a) thawing a container comprising frozen mammalian cells dispersed in the aqueous solution of claim 1 to provide thawed mammalian cells; and (b) adding the thawed mammalian cells to a culture medium suitable for the mammalian cells.

9. The aqueous solution of claim 1, wherein the potassium phosphate comprises monobasic anhydrous potassium phosphate, the sodium phosphate comprises dibasic anhydrous sodium phosphate, the glucose comprises anhydrous D-glucose, the ascorbic acid comprises magnesium-L-ascorbate-2-phosphate, the cysteine comprises L-cysteine hydrochloride monohydrate, or the glutathione comprises reduced glutathione, or any combination thereof.

10. The aqueous solution of claim 1, wherein cysteine and glutathione are the only amino acid compounds in the solution.

11. A method of cryoprotecting cells comprising (a) providing the aqueous solution for cell preservation according to claim 1; and (b) dispersing mammalian cells in the aqueous solution for said cell preservation.

12. The method of claim 11, wherein the method does not include vitrification of the mammalian cells.

13. The method of claim 11, further comprising (c) freezing the mammalian cells, wherein the freezing comprises reducing the temperature at a rate of not greater than 10° C./min.

14. A pharmaceutical product or excipient comprising the aqueous solution of claim 1.

* * * * *